United States Patent [19]
Jerbic

[11] Patent Number: 5,348,614
[45] Date of Patent: Sep. 20, 1994

[54] PROCESS FOR DYNAMIC CONTROL OF THE CONCENTRATION OF ONE OR MORE REACTANTS IN A PLASMA-ENHANCED PROCESS FOR FORMATION OF INTEGRATED CIRCUIT STRUCTURES

[75] Inventor: Chris Jerbic, Cupertino, Calif.

[73] Assignee: LSI Logic Corporation, Milpitas, Calif.

[21] Appl. No.: 80,896

[22] Filed: Jun. 22, 1993

[51] Int. Cl.$^5$ .................. H01L 21/00; G01N 21/00
[52] U.S. Cl. .................... 156/626; 156/643; 156/646; 156/665; 204/192.33; 437/7; 437/8
[58] Field of Search .............. 156/626, 627; 204/298.32, 298.03, 298.37, 298.38, 192.33, 192.13; 118/712, 723; 427/10; 437/7, 8

[56] References Cited

U.S. PATENT DOCUMENTS

| | | | |
|---|---|---|---|
| 4,289,188 | 9/1981 | Mizutani et al. | 156/626 |
| 4,430,151 | 2/1984 | Tsukada | 156/626 |
| 4,457,820 | 7/1984 | Bergeron et al. | 156/626 X |
| 4,704,199 | 11/1987 | Yokokawa et al. | 204/298.03 |

FOREIGN PATENT DOCUMENTS

| | | | |
|---|---|---|---|
| 244847 | 10/1988 | Japan | 156/626 |
| 175740 | 7/1989 | Japan | 156/626 |
| 147555 | 4/1981 | Netherlands | 156/626 |

OTHER PUBLICATIONS

Khoury, "Real-Time Etch Plasma Monitor System", IBM Technical Disclosure Bulletin, vol. 25 No. 11A Apr. 1983.

Auciello, Orlando, et al., "Optical Diagnostic Techniques for Low Pressure Plasmas and Plasma Processing", Plasma Diagnostics, vol. 1, Boston: Academic Press, Inc., 1989, pp. 1–46.

Primary Examiner—Thi Dang
Attorney, Agent, or Firm—John P. Taylor

[57] ABSTRACT

A process for dynamically adjusting the concentration of one or more reactants in a plasma assisted process, such as a plasma etch process or a plasma deposition process, is described. The concentration of one or more reactants, as well as the concentration of a non-reactive gas, in a plasma enhanced process for the formation of an integrated circuit structure is quantitatively monitored by actinometry to derive a ratio of such concentrations of reactant to non-reactant. The concentration of the reactant or reactants in the plasma processing chamber is then maintained in the chamber by adjusting the flow of such reactant or reactants into the chamber based on changes in such ratio based on such continuous quantitative monitoring of the both the concentration of the reactant or reactants and that of the non-reactive (non-changing concentration) component.

6 Claims, 2 Drawing Sheets

PROCESS FOR DYNAMIC CONTROL OF THE CONCENTRATION OF ONE OR MORE REACTANTS IN A PLASMA-ENHANCED PROCESS FOR FORMATION OF INTEGRATED CIRCUIT STRUCTURES

BACKGROUND OF THE INVENTION

1. Field of the Invention

This invention relates to a plasma-enhanced process for forming integrated circuit structures. More particularly, this invention relates to a process for controlling the concentration of the active reactant or reactants in a reaction chamber during plasma processing to form an integrated circuit structure on a substrate such as a semiconductor wafer.

2. Description of the Related Art

During the plasma processing of a substrate such as a semiconductor wafer to form an integrated circuit structure thereon, the reactant or reactants concentration in the reaction chamber may become depleted during a plasma etch (or plasma deposition). For example, in a plasma etch process using chlorine as the reactive species to etch a pattern in a metal layer such as aluminum, the density of the lines for a particular integrated circuit structure being formed may vary widely from the pattern of another integrated circuit structure. This, in turn, can lead to a depletion of the chlorine reactant during the etch of some integrated circuit structures, due to the excessive amount of metal being etched away for the particular structure. Such a depletion of chlorine can lower the etch rate, result in an increase in etch residues, change the shape of the aluminum lines being formed, and change the selectivity of the etchant for the resist mask.

Conventionally, the concentration of the active reactant (or reactants) for etching and/or deposition processes has been controlled by controlling the flow rate of the reactant or reactants into the chamber by a previous empirical determination of the flow rate needed for a particular etch or deposition process for an average integrated circuit structure. Rather than attempt to empirically determine the required modifications to such a process (the change in flow rates of reactants) needed for each individual integrated circuit structure being processed, attempts have been made, instead, to modify the particular structure being processed to arrive at an average pattern density.

If, for example, the pattern density of the metal lines in a particular desired structure is below about 30%, a fill material is sometimes added to provide dummy metal lines to that particular integrated circuit structure to make it more closely resemble the "average" structure for which the process was designed. This addition of dummy lines will, thereby, adjust the amount of metal being etched away to more closely resemble the average amount for which the flow rates of etchant in the etch process were determined. In this manner, the degree or amount of variation in density from one structure to another is reduced and the amount of depletion of the reactant (etchant in this case) for a particular structure will be correspondingly reduced, thus enabling one to use the predetermined reactant flow rate to maintain the concentration of reactant (e.g., etchant) in the reactor.

However, such a remedy is less than satisfactory. The amount of such fill material which can be added to a given integrated circuit pattern is limited, and therefore, the amount of the reduction in the variation of pattern density achievable with this method is limited. Furthermore, the presence of the fill material can be deleterious in some instances. For example, in the aforementioned plasma chlorine etch of a metal layer to form a pattern of metal lines, the addition of further dummy metal lines into the pattern, as fill material, adds further conductive material to the pattern. This, in turn, can raise the chances of a short or other defect occurring.

The addition of such fill in material also complicates mask design and manufacture, and limits the ability to use masks and patterns not specifically designed by the manufacturer (processor) of the integrated circuit structure to accommodate the particular process to be carried out.

It would, therefore, be desirable to be able to provide a process for the formation of integrated circuit structures wherein the concentration of one or more active reactants being used in a plasma etch or a plasma deposition could be monitored and dynamically adjusted throughout the process to thereby avoid the above-discussed undesirable depletion of the reactant or reactants during the process. This, in turn, would free the processing from dependence upon the density of the pattern being etched or deposited for satisfactory operation of the process.

SUMMARY OF THE INVENTION

It is, therefore, an object of this invention to provide a process for monitoring the concentration of one or more active reactants being used in a plasma etch or a plasma deposition, and adjusting such concentration throughout the process to avoid undesirable depletion of the reactant or reactants during the plasma etch or deposition in the formation of a particular integrated circuit structure.

In accordance with the invention, the concentration of one or more reactants, as well as the concentration of a non-reactive gas, in a plasma enhanced process for the formation of an integrated circuit structure, is quantitatively monitored by actinometry to derive a ratio of such concentrations. The concentration of the reactant or reactants in the plasma processing chamber is then maintained in the chamber by adjusting the flow of such reactant or reactants into the chamber based on sensed changes in such ratio based on such continuous quantitative monitoring of the both the concentration of the reactant or reactants and that of the non-reactive (non-changing concentration) component.

DETAILED DESCRIPTION OF THE INVENTION

Figure 1:
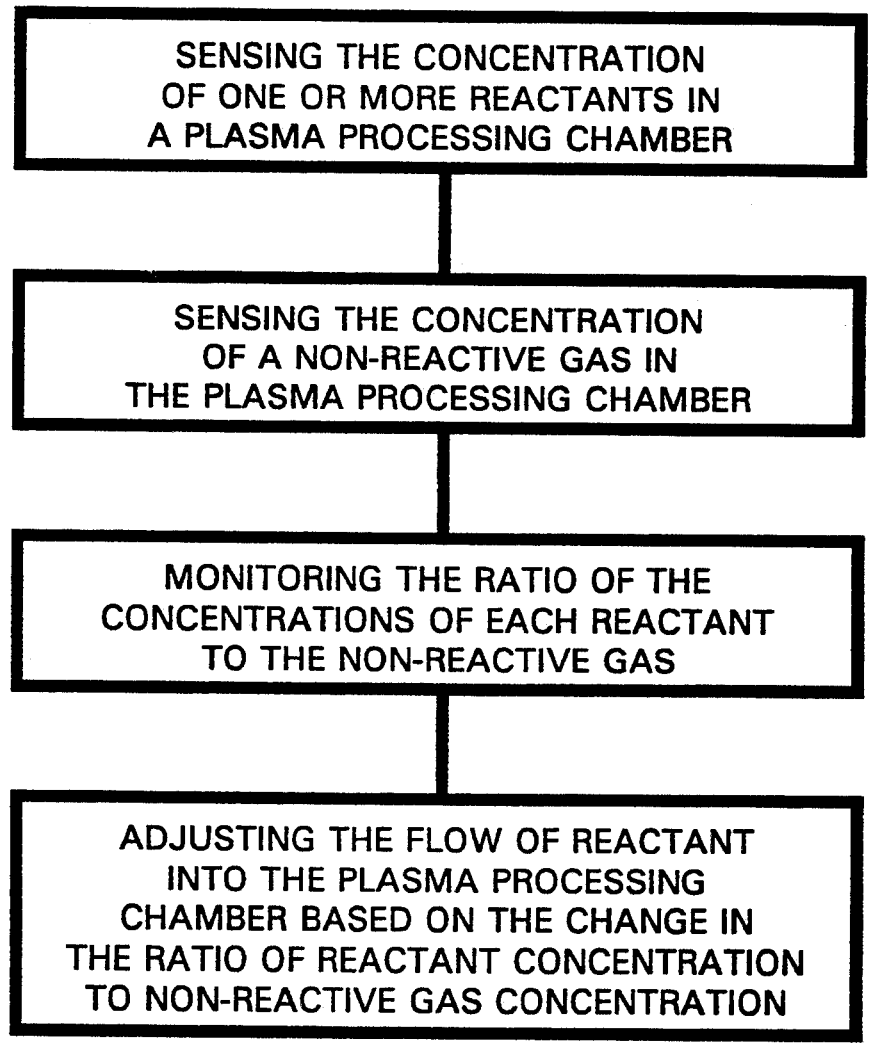
FIG. 1 is a flow sheet illustrating the process of the invention.
Figure 2:
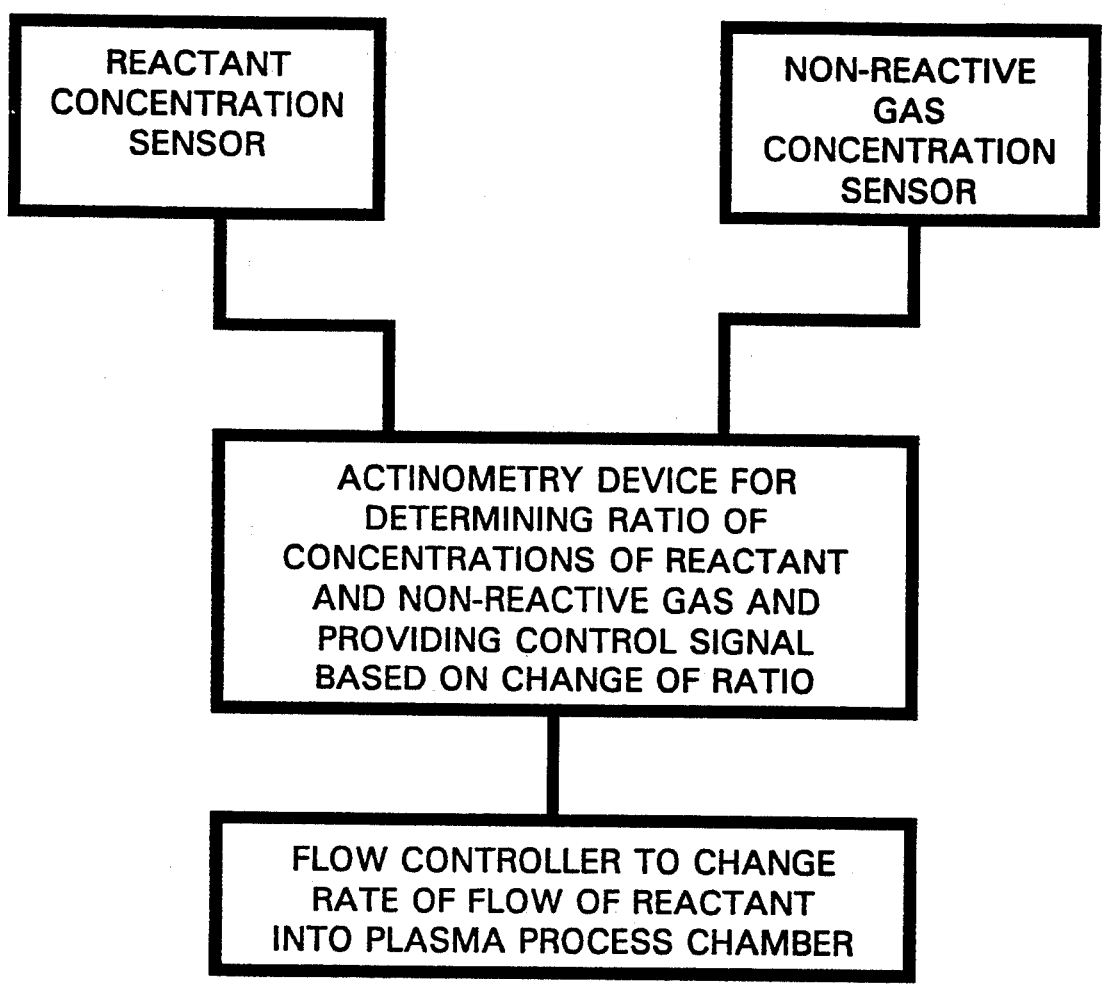
FIG. 2 is a diagrammatic depiction of the apparatus used in practicing the process of the invention.

The invention comprises a process for controlling the concentration of one or more reactants in a plasma enhanced process for the formation of an integrated circuit structure using measurements of the respective optical emissions of an inert species and an active species (reactant) to monitor the change in concentration of such one or more reactants in a plasma processing chamber, and then adjusting the flow of such reactant or reactants into the chamber based on such monitoring of the concentration of the reactant or reactants in the chamber. Such measurements of the respective emissions of an inert species and an active species are referred to as actinometry. Actinometry is described in more detail on pages 9–13 of Chapter 1 of Plasma Diagnostics, Volume 1, edited by O. Auciello and D. Flamm, published by Academic Press in San Diego, Calif. in 1989.

The process of the invention then, comprises quantitatively measuring the optical emission of two or more components in a plasma in a processing chamber on a continuous basis, wherein one of the monitored components is a non-depleting, i.e., non-reactive, component, while the other is a reactive component. A ratio of the measured concentrations is then obtained; this ratio is monitored for a change, indicative of a change in the concentration of the reactive component; and then, using an emitted signal indicating a positive or negative change in this ratio, changing the set point on a flow controller for that reactive component in the plasma to increase or decrease the flow of this reactive component into the processing chamber to return the ratio back to a predetermined point. It should be noted that while measurement of the optical emission of the components of the plasma is preferred, it is within the scope of the invention to measure the concentration of the plasma components by other parameters of the plasma such as by absorption spectroscopy.

By optically sensing the concentration of one of the reactants being consumed in the plasma enhanced process in the chamber with one sensor, and optically sensing the concentration of a non-reactive component in the processing chamber with the other sensor, the ratio thereby obtained is an indication of the concentration of the consumable reactant in the chamber which is relatively free of noise. This is because the noise, such as a dirty window through which the optical emissions are sensed, will effect both the measurement of the consumed reactant as well as the non-reactive component, thereby effectively cancelling out the noise.

The process may be used to control the concentration of more than one reactant in a process by providing a separate sensor for each reactive component which is being consumed in the plasma enhanced process, i.e., each reactant. The quantitative optical emission signal for each such reactant is then compared with the quantitative optical emission signal of a non-reactive component in the chamber to thereby derive the desired ratio. Separate signals for each such monitored ratio would then be fed, respectively, to separate flow controllers for the corresponding reactant to thereby increase (or decrease, if needed) the concentration of that reactant in response to the change in the ratio of that reactant with the non-reactive component.

By use of the term "non-reactive" component is meant a material being flowed into the plasma chamber which is not consumed by the plasma-enhanced etching or deposition process and which may or may not enter into the formation of the plasma, but which will be excited by the plasma to thereby emit a measurable optical signal indicative of the concentration of the non-reactive component in the chamber. Usually such a non-reactive component will comprise an inert carder gas such as argon or helium. A very small amount of such inert carrier gas is needed, i.e., about 5–15 sccm.

Actinometry equipment is commercially available, for example, from EG&G Princeton Applied Research, which manufactures a single spectrometer with multiple wavelength sensing of up to 512 wavelengths simultaneously using sensors with appropriate filters. Such equipment has been used to sense the endpoint of a plasma assisted process, such as a plasma etch process by sensing for the appearance, or disappearance, of certain wavelengths emitted by a particular species.

Such equipment provides an output signal which may be fed to a commercially available flow controller such as, for example, a Tylan General FC-280 flow controller available from the Tylan General Company, to change the set point thereof, i.e., to increase or decrease the flow into the reactor of the particular reactant being sensed.

It should be noted that the process of the invention may be used to monitor and dynamically control the concentration in the reactor of more than one reactant, by using a separate sensor for each reactant for which one wishes to monitor and adjust the concentration in the reactor, with a single control sensor used to monitor the non-reactive component in the reactor with the signal from that sensor providing the comparison signal which can then be used to derive the respective ratio signal for each of the reactive components being monitored. Of course, when multiple reactive components are to be monitored, separate flow controllers will be used for each of such reactive components and a separate signal will be sent from the actinometry apparatus to each of these flow controllers.

While it is believed that the process of the invention may be used with any plasma-enhanced process, including both plasma etch and plasma deposition process, the invention may be of particular value in back end processing such as the patterning of metal or polysilicon wiring harnesses or in the formation of contact or via openings, i.e., etching openings in oxide, since such back end processing may vary widely from wafer to wafer because of the difference in the design structure or circuitry to be applied to the integrated circuits structures on the various wafers, as such are customized for the individual use by various customers from generic gate array structures initially formed on the wafers.

Thus, by way of illustration, and not of limitation, when an aluminum layer is patterned to form a series of metal lines comprising a wiring harness, after formation of a photoresist mask thereon, the aluminum layer is plasma etched by typically flowing about 50 standard cubic centimeters per minute (sccm) of chlorine, and about 10 sccm of argon into a vacuum chamber maintained at a pressure of about 5–500 Torr and a temperature of about 100° C., while maintaining a plasma in the chamber at a power level of about 300 watts. The aluminum is etched, by the reaction of the chlorine with the aluminum, and the above-mentioned flow is designed to be adequate for an average density of aluminum to be etched of about 30% of the entire aluminum layer.

In accordance with the invention, however, the emission of one of the wavelengths of the chlorine atoms and/or ions excited in the plasma, such as the 840 nm wavelength, is quantitatively monitored with a sensor having a filter thereon to screen out other wavelengths, while the emission of the excited, but non-reactive, argon atoms and/or ions in the plasma is also quantitatively monitored by a selectively filtered sensor, with the output of both sensors fed to the actinometry apparatus. The actinometry apparatus derives a ratio of the two signals and then monitors this ratio for change. When the ratio of sensed chlorine concentration to sensed argon concentration drops, indicating that less chlorine is now present in the reactor (compared to argon) than previously, an output signal from the actinometry apparatus is sent to the chlorine flow controller to raise the set point thereof, i.e., to increase the flow of chlorine into the reactor. When the chlorine:argon ratio then rises, the set point of the flow controller is appropriately reduced. This constant "on the fly" or dynamic monitoring and adjustment of the chlorine concentration in the reactor is then carried out throughout the etch process until the process is finished.

In this manner, in accordance with the invention, the concentration of the reactive component (in this case chlorine) remains constant throughout the process, regardless of the density of the material to be etched, and without having to adjust the mask or pattern to provide dummy fill areas to attempt to adjust a low density pattern (large amount to be etched) back to a normal or average etch density. The problems associated with low or high density patterns, as well as the problems associated with some of the prior art remedies for such low or high density patterns, can therefore be avoided with the dynamic monitoring technique of the invention.

Similarly, the concentration of, for example, carbon-fluorine radicals (e.g., $CF$, $CF_2$, or $CF_3$) may be quantitatively monitored during the etching of an oxide layer to form openings therein for vias or contacts, while the concentration of, for example, nitrogen, could be quantitatively monitored during the reactive sputter deposition of a layer of titanium nitride onto an integrated circuit structure.

While specific embodiments of the process of the invention have been illustrated and described, modifications and changes of the process, including various process apparatus variations, process parameters, and materials, etc. will become apparent to those skilled in the art, and it is intended to cover in the appended claims all such modifications and changes which come within the scope of the invention.

Having thus described the invention what is claimed is:

1. In a plasma etch process for etching various aluminum patterns on integrated circuit structures on semiconductor wafers in a plasma etching chamber, wherein the amount of aluminum to be removed will vary from wafer to wafer, depending upon the particular aluminum pattern to be etched, resulting in the need for a change in flow rate of etchant gas into said etching chamber from wafer to wafer, to thereby control the concentration of said etchant gas in said etching chamber, the improvement which comprises:
   a) loading into a plasma etch chamber a semiconductor wafer having an integrated circuit structure formed thereon including an aluminum layer having a mask thereon to define a desired pattern of aluminum on said structure;
   b) flowing into said plasma etch chamber a mixture of an etchant gas capable of plasma etching aluminum and a non-reactive gas;
   c) igniting a plasma in said chamber to plasma etch said masked aluminum layer;
   d) monitoring the respective optical emissions of said non-reactive gas and said aluminum etchant gas during said etch to determine the amount of said aluminum etchant gas being consumed by said aluminum; and
   e) changing the flow of said aluminum etchant gas into said plasma etch chamber to match the amount of etchant gas being consumed by the portions of said aluminum exposed by said mask;

whereby the concentration of aluminum etchant gas in said chamber will remain constant during said etch regardless of the amount of aluminum being etched to provide the particular aluminum pattern desired for a particular integrated circuit structure.

2. The process of claim 1 wherein said aluminum etchant gas is a chlorine etching gas.

3. The process of claim 2 wherein said non-reactive gas is selected from the group consisting of argon and helium.

4. The process of claim 3 wherein said amount of said flow of such non-reactive gas into said plasma etch chamber ranges from about 5–15 sccm.

5. The process of claim 4 where the ratio of said chlorine etching gas to said non-reactive gas is about 5:1.

6. In a plasma etch process for etching various aluminum patterns on integrated circuit structures on semiconductor wafers in a plasma etching chamber, wherein the amount of aluminum to be removed will vary from wafer to wafer, depending upon the particular aluminum pattern to be etched, resulting in the need for a change in flow rate of etchant gas into said etching chamber from wafer to wafer, to thereby control the concentration of said etchant gas in said etching chamber, the improvement which comprises:
   a) loading into a plasma etch chamber a semiconductor wafer having an integrated circuit structure formed thereon including an aluminum layer having a mask thereon to define a desired pattern of aluminum on said structure;
   b) flowing into said plasma etch chamber a mixture of a chlorine etchant gas capable of plasma etching aluminum, and a non-reactive gas selected from the group consisting of argon and helium in an initial flow ratio of about 5:1;
   c) igniting a plasma in said chamber to plasma etch said masked aluminum layer;
   d) monitoring the respective optical emissions of said argon or helium non-reactive gas and said chlorine etching gas during said etch and comparing the ratio of emission intensities to an initial ratio of emission intensities to determine the amount of said aluminum etchant gas being consumed by said aluminum; and
   e) changing the flow of said chlorine etching gas into said plasma etch chamber to match the amount of etchant gas being consumed by the portions of said aluminum exposed by said mask;

whereby the concentration of aluminum etchant gas in said chamber will remain constant during said etch regardless of the amount of aluminum being etched to provide the particular aluminum pattern desired for a particular integrated circuit structure.

* * * * *